US012566184B2

(12) United States Patent
Styczynski et al.

(10) Patent No.: US 12,566,184 B2
(45) Date of Patent: Mar. 3, 2026

(54) CELL-FREE BIOSENSORS TO DETECT CREATININE, CREATINE, AND SARCOSINE

(71) Applicant: Georgia Tech Research Corporation, Atlanta, GA (US)

(72) Inventors: Mark Styczynski, Atlanta, GA (US); Elizabeth Hutson Chilton, Atlanta, GA (US); Emily Heckard, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 776 days.

(21) Appl. No.: 17/937,968

(22) Filed: Oct. 4, 2022

(65) Prior Publication Data

US 2023/0109434 A1 Apr. 6, 2023

Related U.S. Application Data

(60) Provisional application No. 63/251,757, filed on Oct. 4, 2021.

(51) Int. Cl.
| | |
|---|---|
| *C12Q 1/68* | (2018.01) |
| *G01N 21/78* | (2006.01) |
| *G01N 33/70* | (2006.01) |
| *G01N 33/96* | (2006.01) |

(52) U.S. Cl.
CPC ............. *G01N 33/70* (2013.01); *G01N 21/78* (2013.01); *G01N 33/96* (2013.01)

(58) Field of Classification Search
CPC .................................. C12Q 1/68; C12N 15/00
USPC .............................................................. 435/6
See application file for complete search history.

(56) References Cited

FOREIGN PATENT DOCUMENTS

| | | | | |
|---|---|---|---|---|
| CN | 102579323 A | * | 7/2012 | |
| WO | WO-2020051268 A1 | * | 3/2020 | ............. G01N 21/78 |

OTHER PUBLICATIONS

Willsey & Wargo, Sarcosine Catabolismin Pseudomonas aeruginosa Is Transcriptionally Regulated by SouR, J Bacteriol. Oct. 26, 2015;198(2):301-10. doi: 10.1128/JB.00739-15. Print Jan. 15, 2016.*

* cited by examiner

*Primary Examiner* — Aaron A Priest
(74) *Attorney, Agent, or Firm* — TROUTMAN PEPPER LOCKE LLP; Ryan A. Schneider; Dustin B. Weeks

(57) ABSTRACT
An exemplary embodiment of the present disclosure provides a biosensor that can facilitate detection of the molecules creatinine, creatine and/or sarcosine in a minimal-equipment, portable, and low-cost fashion. Some aspects of the disclosure relate to methods and systems to enable quantitative measurement of certain biomarkers at the point of care without expensive instrumentation.

17 Claims, 15 Drawing Sheets

<u>200</u>

CELL-FREE BIOSENSORS TO DETECT CREATININE, CREATINE, AND SARCOSINE

CROSS-REFERENCE TO RELATED APPLICATIONS

This application claims the benefit of U.S. Provisional Application Ser. No. 63/251,757, filed on 4 Oct. 2021, which is incorporated herein by reference in its entirety as if fully set forth below.

FEDERALLY SPONSORED RESEARCH STATEMENT

This invention was made with government support under grant/award number U54EB027049 awarded by the National Institutes of Health. The government has certain rights in the invention.

FIELD OF THE DISCLOSURE

Embodiments of the present invention relate generally to systems and methods for quantifying analytes in a desired complex solution with minimal inter-sample variability, and more specifically to methods and diagnostic tools for quantifying creatinine, creatine and/or sarcosine in aqueous solutions or biological fluid samples with sample-specific calibration and colorimetric or detectable output.

BACKGROUND

Most diagnostics, particularly those adapted for blood analytics, are complex assays that require highly-trained staff and sophisticated analytical equipment, resulting in high per-sample costs and long waiting times for results. Simple, low-cost diagnostics from small blood sample volumes are needed to avoid these issues. Cell-free expression (CFE) systems, comprising cell extracts supplemented with additional chemical resources, can be a particularly promising approach to fulfill this potential. In particular, their low cost, ease of use, small reaction volumes, and ability to be stably stored and shipped in a lyophilized, freeze-dried format make cell-free expression systems appealing for use in almost any setting (from field studies to at-home use), with minimal or no equipment required. To date, however, equipment-free cell-free expression-based diagnostics have been limited only to presence/absence detection (not quantification), and only to diseases with nucleic acid biomarkers. Importantly, the overwhelming majority of clinically relevant biomarkers for conditions beyond infectious disease are not nucleic acids, and for these biomarkers, quantification of their concentrations is important.

Quantitative measurement of biomarkers and other analytes in complex samples is inherently difficult to do robustly, and even more so when constrained to a minimal-equipment framework. Variability in the components of complex samples like biological fluids or water can affect the readouts of even sophisticated analytical instrumentation, a phenomenon known as "matrix effects" that can yield inaccurate results. In a system with minimal equipment and no mechanisms to compensate for sample-to-sample variability, these matrix effects may be substantial and could preclude the use of standard quantification approaches like calibration curves made from chemical standards, thus hindering development of quantitative diagnostics.

What is needed, therefore, is a quantitative diagnostic system and method that reduces or eliminates inter-sample variability in measuring analytes with complex samples such as biological fluids and water. The diagnostic system and method should enable sample-specific calibration to reduce or eliminate such variability and provide a generalizable parallel calibration strategy. It is to such a system and method that embodiments of the present invention are directed.

The ability to quantitatively measure the levels of specific small molecules in biofluid specimens (e.g., blood or urine) would provide clinically important diagnostic information that could inform treatment plans.

BRIEF SUMMARY

In an exemplary embodiment of the present disclosure, there is provided a method of generating a diagnostic tool for measuring an unknown amount of an analyte in a biological sample using a cell-free extract (CFE). The method can include: determining a desired amount of a regulator of a reporter, determining a saturating amount of the analyte, and determining a desired reaction time. The diagnostic tool can include a plurality of reference points, each reference point being a distinct color and corresponding to a different amount of the analyte. The desired amount of the regulator of the reporter, the saturating amount of the analyte, and the desired reaction time can be determined such that when the unknown amount of the analyte is combined with the biological sample, the CFE, and the desired amount of the regulator of the reporter for the desired reaction time, a colorimetric gene product is generated having a color corresponding to a color of a first reference point in the plurality of reference points containing the biological sample, the CFE, the saturating amount of analyte, and the desired amount of the regulator of the reporter, the first reference point associated with an amount of the analyte about equal to the unknown amount of analyte.

In some embodiments, the method can further include obtaining a plurality of outputs from a plurality of varying levels of the regulator and comparing the plurality of outputs to a plurality of outputs from a plurality of varying levels of analyte at a fixed level of regulator.

In some embodiments, the biological sample is one or more of: blood, serum, plasma, urine, saliva, tears, mucus, lymph, interstitial fluid, cerebrospinal fluid, pus, breast milk, and amniotic fluid.

In some embodiments, the analyte can include one of creatinine, creatine, or sarcosine.

An exemplary embodiment of the present invention discloses a method for generating a range of visible colors in serum samples with unknown amounts of an analyte by addition of a small molecule, wherein the small molecule displaces an interfering molecule from one or more of a regulator, a reporter, and a molecule acted on by the reporter.

The method can include determining a desired amount of a regulator of a reporter, determining a saturating amount of the analyte, and determining a desired reaction time. The desired amount of the regulator of the reporter, the saturating amount of the analyte, and the desired reaction time can be determined such that when the unknown amount of the analyte is combined with the serum and the desired amount of the regulator of the reporter for the desired reaction time, a colorimetric gene product is generated having a color corresponding to a color of a first reference point in a plurality of reference points containing the serum, the saturating amount of analyte, and the desired amount of the regulator of the reporter, the first reference point associated with an amount of the analyte about equal to the unknown amount of analyte. The method can be configured to reduce or eliminate inter-sample variability.

In some embodiments, the reporter can include a linear fragment of DNA, the linear fragment of DNA can include the regulator and a reporter gene operatively linked to a genetic element that is regulated by the regulator.

In some embodiments, the reporter can include a first plasmid containing a transcriptional regulator and a second plasmid containing a reporter gene operatively linked to a promoter, wherein expression from the promoter is controlled by the amount of the regulator.

In some embodiments, the method can further include converting via an enzyme the analyte, wherein the converted analyte is configured to allow binding of the regulator and the promoter thus activating transcription of the reporter gene.

In some embodiments, the analyte can include one of creatinine, creatine, or sarcosine.

In some embodiments, the regulator of the reporter can include a sarcosine-responsive transcription factor from *Pseudomonas aeruginosa* (SouR).

An exemplary embodiment of the present invention discloses a method for generating a range of visible colors in serum samples with unknown amounts of an analyte by addition of a small molecule, wherein the small molecule displaces an interfering molecule from one or more of a regulator, a reporter, and a molecule acted on by the reporter. The method can include providing a desired amount of a regulator of a reporter, providing a saturating amount of the analyte, providing a desired reaction time, and stabilizing the reporter. The desired amount of the regulator of the reporter, the saturating amount of the analyte, and the desired reaction time can be determined such that when the unknown amount of the analyte is combined with the serum, and the desired amount of the regulator of the reporter for the desired reaction time, the reporter generates a color corresponding to a color of a first reference point in the plurality of reference points containing the serum, the saturating amount of analyte, and the desired amount of the regulator of the reporter, the first reference point associated with an amount of the analyte about equal to the unknown amount of analyte. The method can be configured to reduce or eliminate inter-sample variability.

In some embodiments, the reporter comprises a limited chemical probe.

In some embodiments, the chemical probe can include a fluorogenic peroxidase substrate.

In some embodiments, the reporter can include a linear fragment of DNA, the linear fragment of DNA including the regulator and a reporter gene operatively linked to a genetic element that is regulated by the regulator.

In some embodiments, the reporter can include a first plasmid containing a transcriptional regulator and a second plasmid containing a reporter gene operatively linked to a promoter, wherein expression from the promoter is controlled by the amount of the regulator.

In some embodiments, the method can further include converting 310 via an enzyme the analyte, wherein the converted analyte is configured to allow binding of the regulator and the promoter thus activating transcription of the reporter gene.

In some embodiments, the analyte can include one of creatinine, creatine, or sarcosine.

In some embodiments, the regulator of the reporter can include a sarcosine-responsive transcription factor from *Pseudomonas aeruginosa* (SouR).

In some embodiments, stabilizing the reporter can include providing a stabilizing compound.

In some embodiments, the stabilizing compound can include one or more of: doxorubicin, vitamin C, citric acid, vitamin E, uric acid, L-glutathione (reduced), and (±) Hydroxy-2,5,7,8-tetramethylchromane-2-carboxylic acid.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

DETAILED DESCRIPTION

Figure 1:
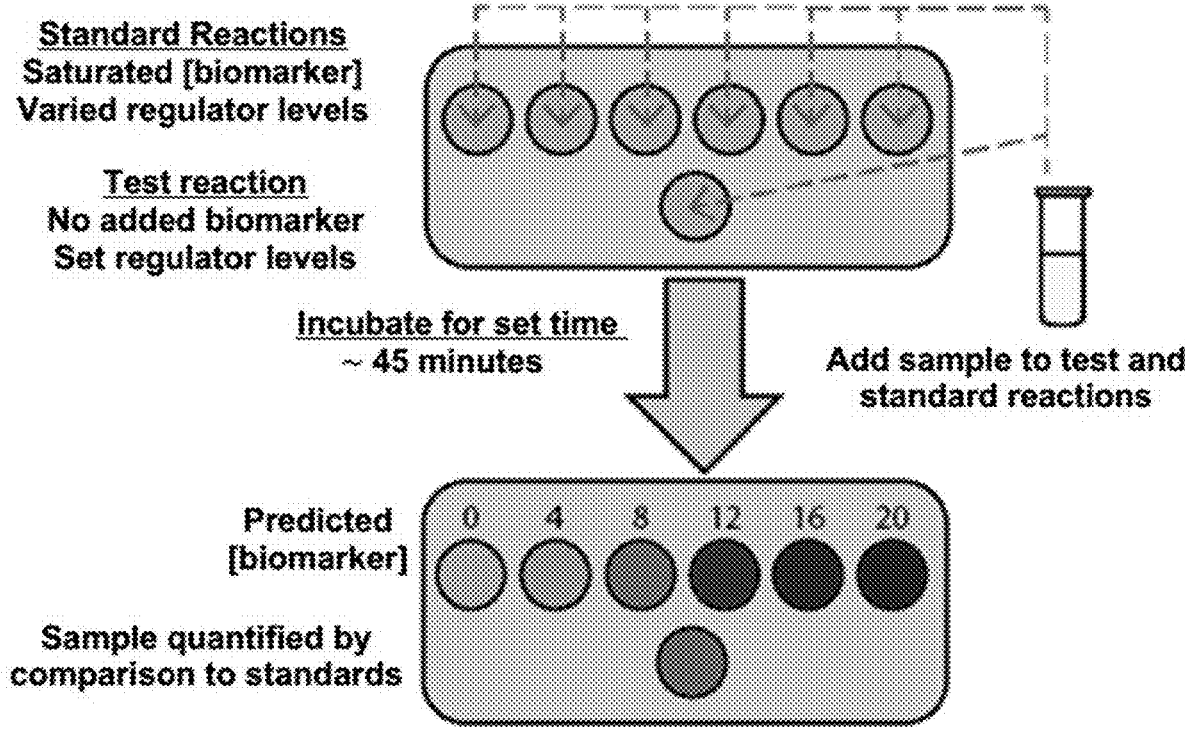
FIG. 1 illustrates a schematic of standardization method to account for matrix effects. An array of standard reactions had saturated biomarker concentrations and varied regulator concentrations. The test reaction had a set regulator concentration and no added biomarker. The sample to be analyzed was added to both the standard and test reactions so that all reactions run in the same sample matrix. After a set incubation time, the color of the test reaction can be matched to the color of the standard reactions to determine biomarker concentration in the test reaction.
Figure 2:
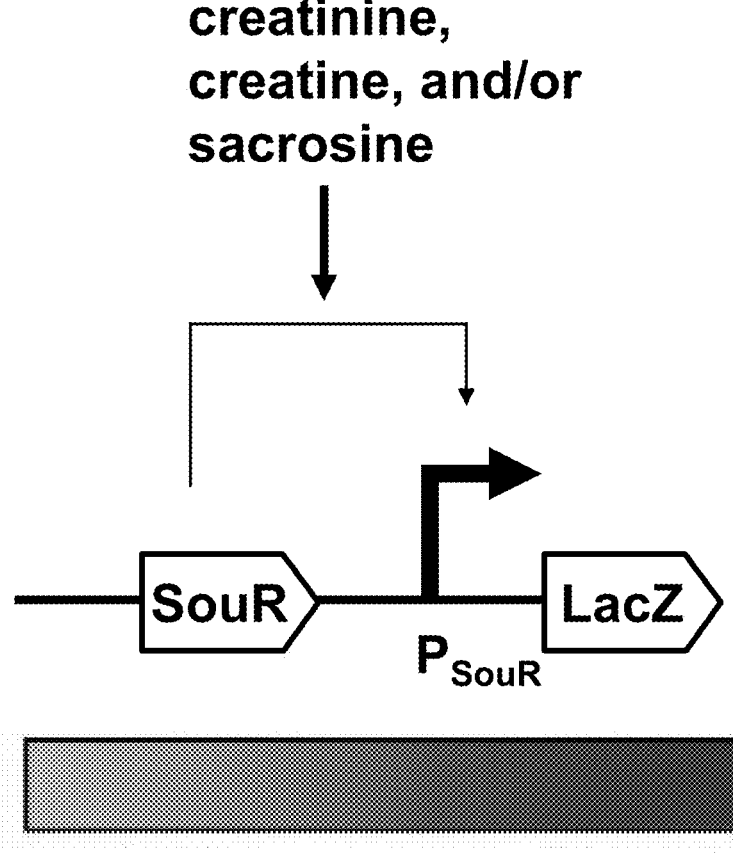
FIG. 2 is a schematic of an exemplary sarcosine-responsive circuit used to control β-galactosidase production. β-galactosidase is expressed from the SouR-regulated promotor.
Figure 3:
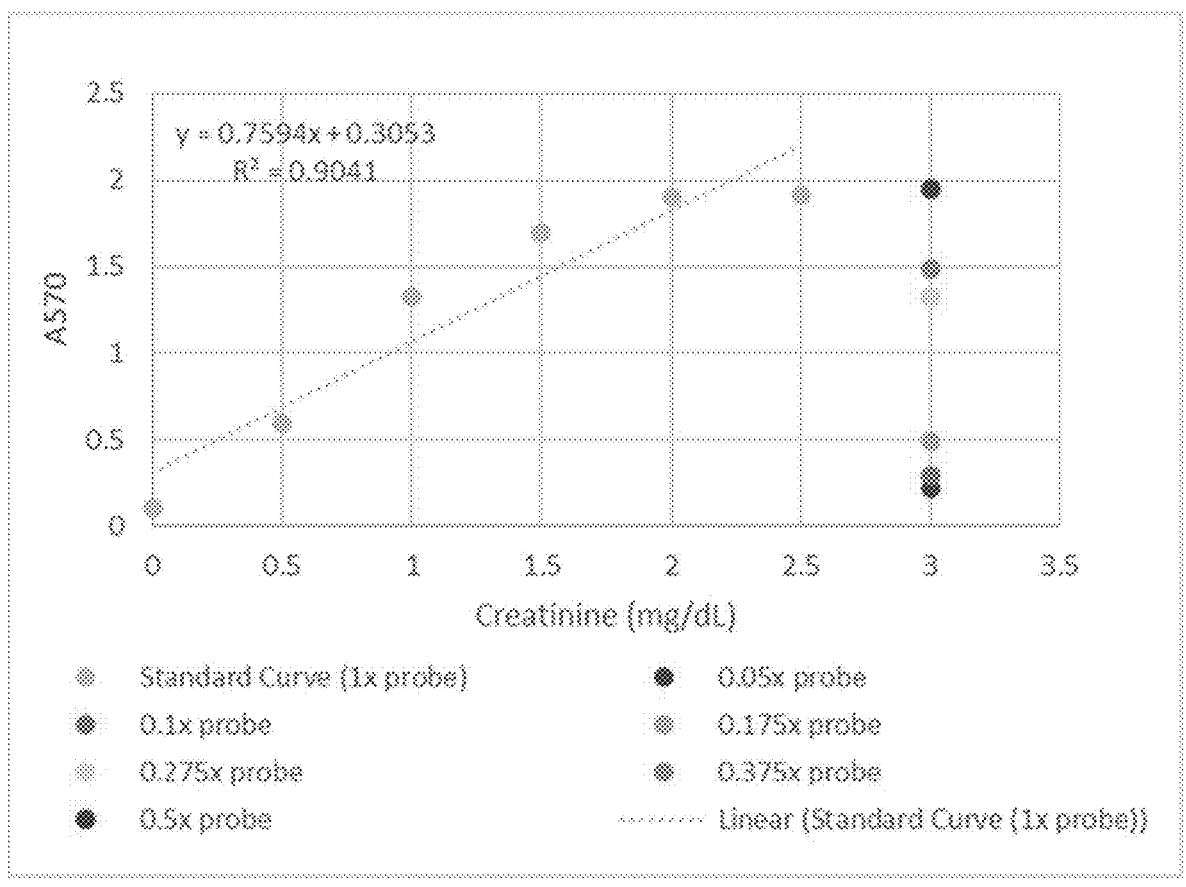
FIG. 3 illustrates an example linear dynamic range of an enzymatic assay, in accordance with an exemplary embodiment of the present invention.
Figure 4:
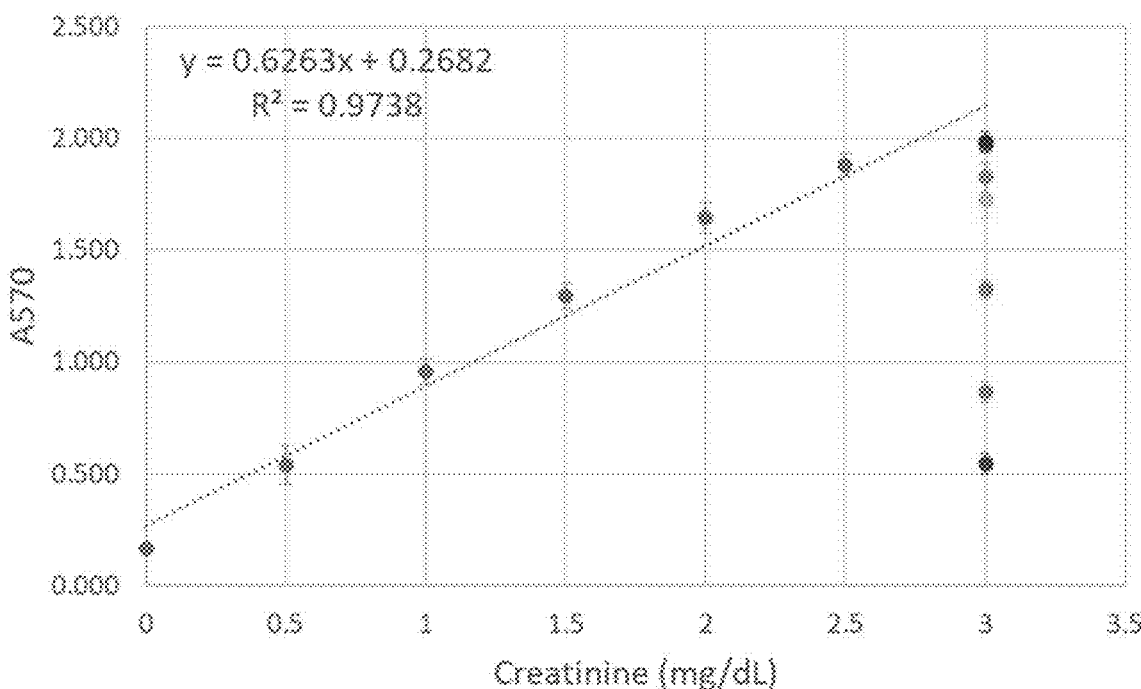
FIG. 4 illustrates an example linear dynamic range of an enzymatic assay, in accordance with an exemplary embodiment of the present invention.
Figure 5:
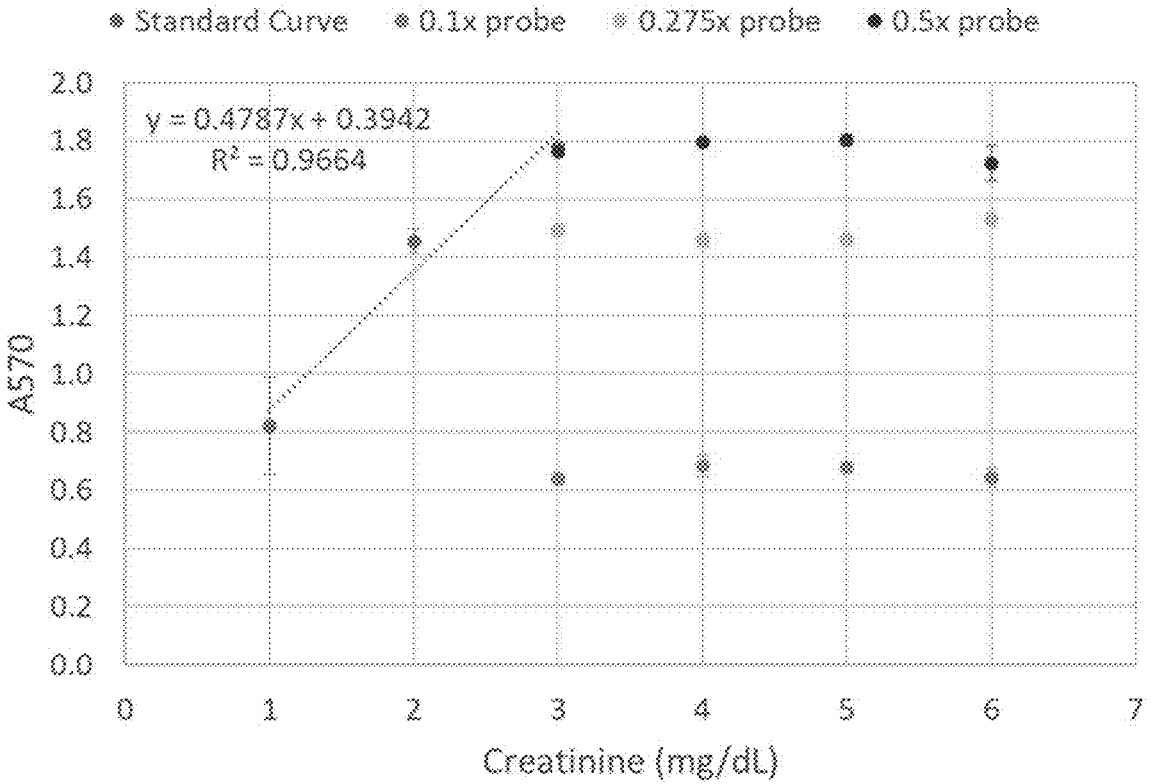
FIG. 5 illustrates absorbance values at different concentrations of an analyte for various concentrations of a probe, in accordance with an exemplary embodiment of the present invention.
Figure 6:
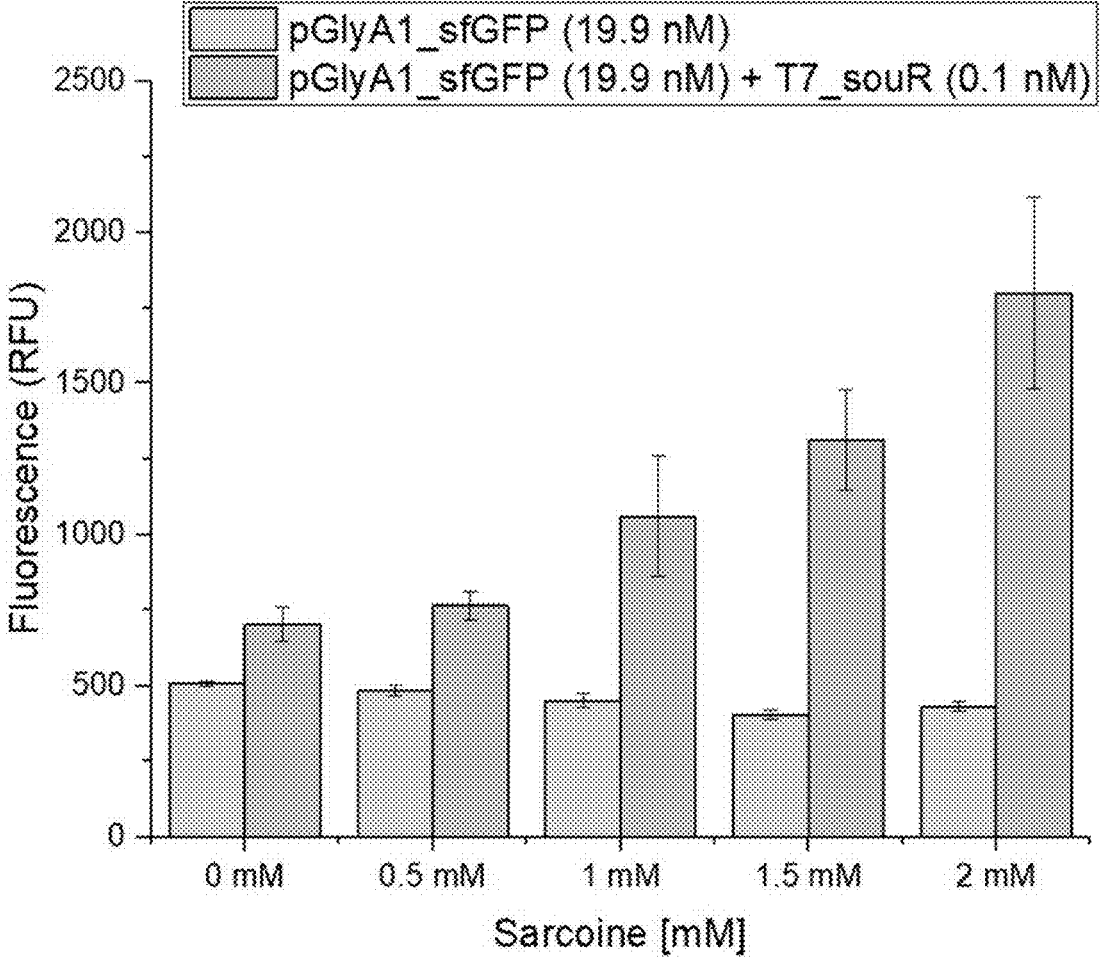
FIG. 6 illustrates fluorescence values at various concentrations of analyte, in accordance with an exemplary embodiment of the present invention.
Figure 7:
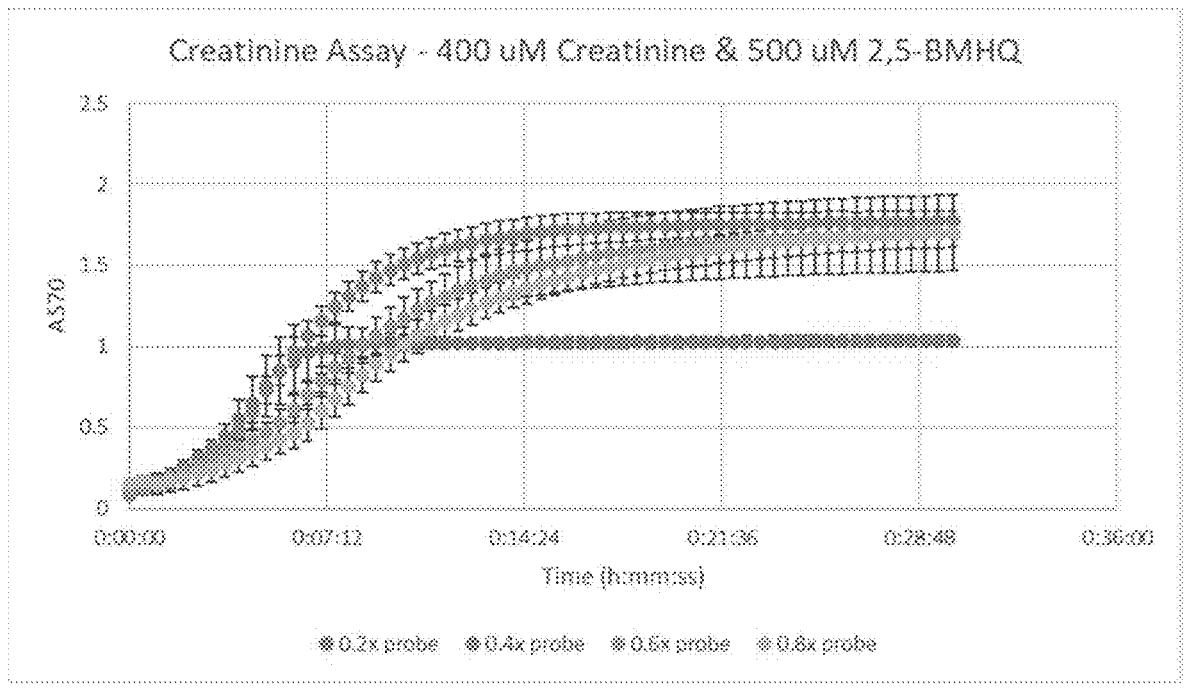
FIG. 7 illustrates stabilization of absorbance/reporter, in accordance with an exemplary embodiment of the present invention.
Figure 8:
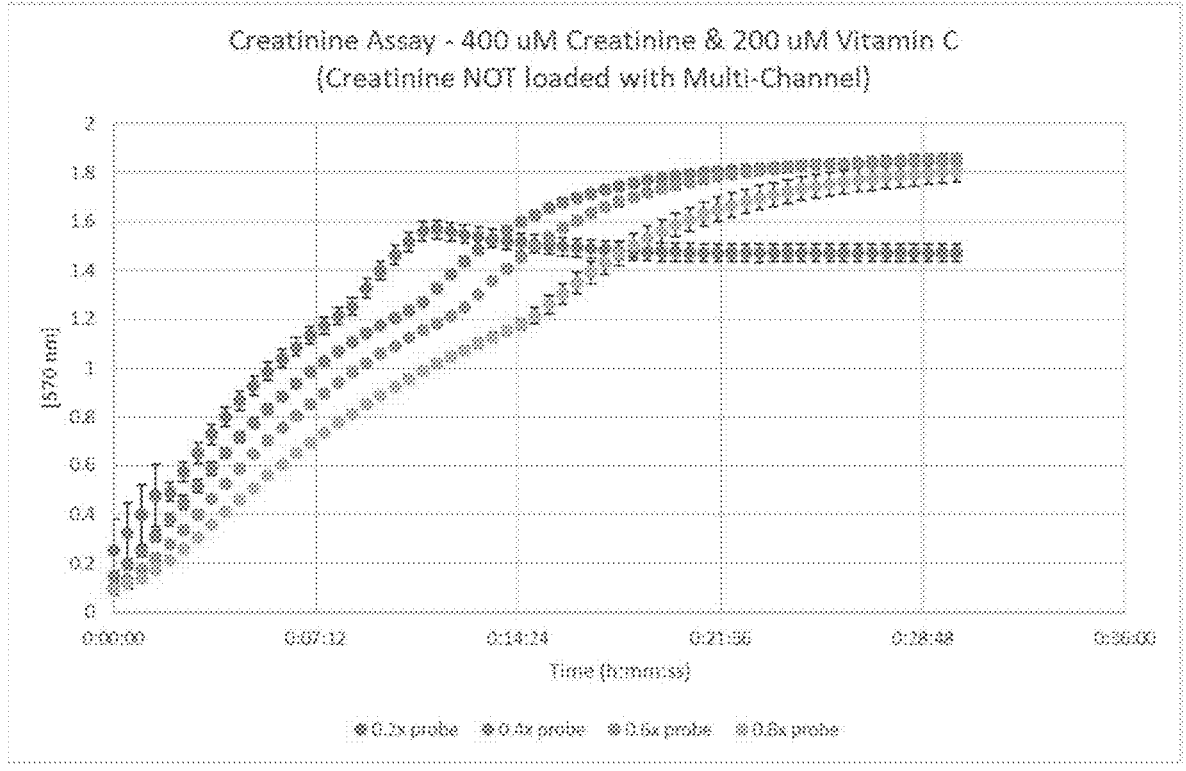
FIG. 8 illustrates stabilization of absorbance/reporter, in accordance with an exemplary embodiment of the present invention.
Figure 9:
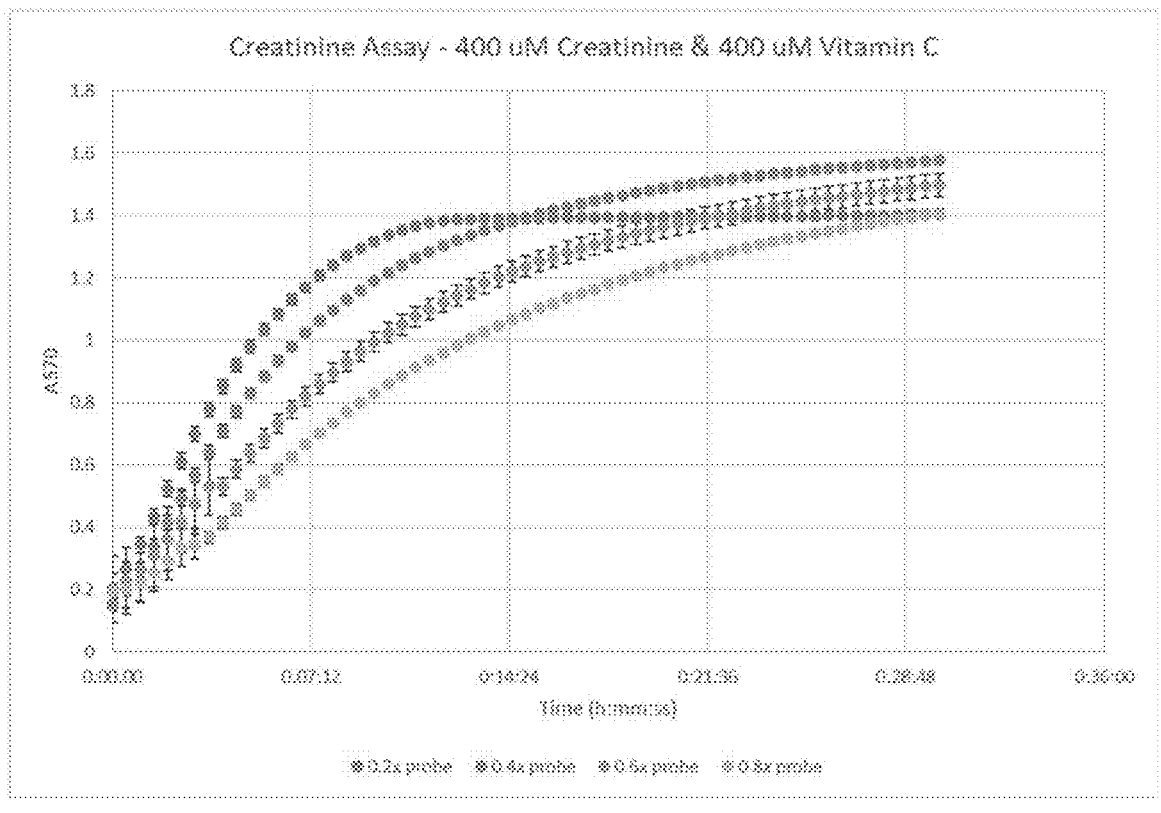
FIG. 9 illustrates stabilization of absorbance/reporter, in accordance with an exemplary embodiment of the present invention.
Figure 10:
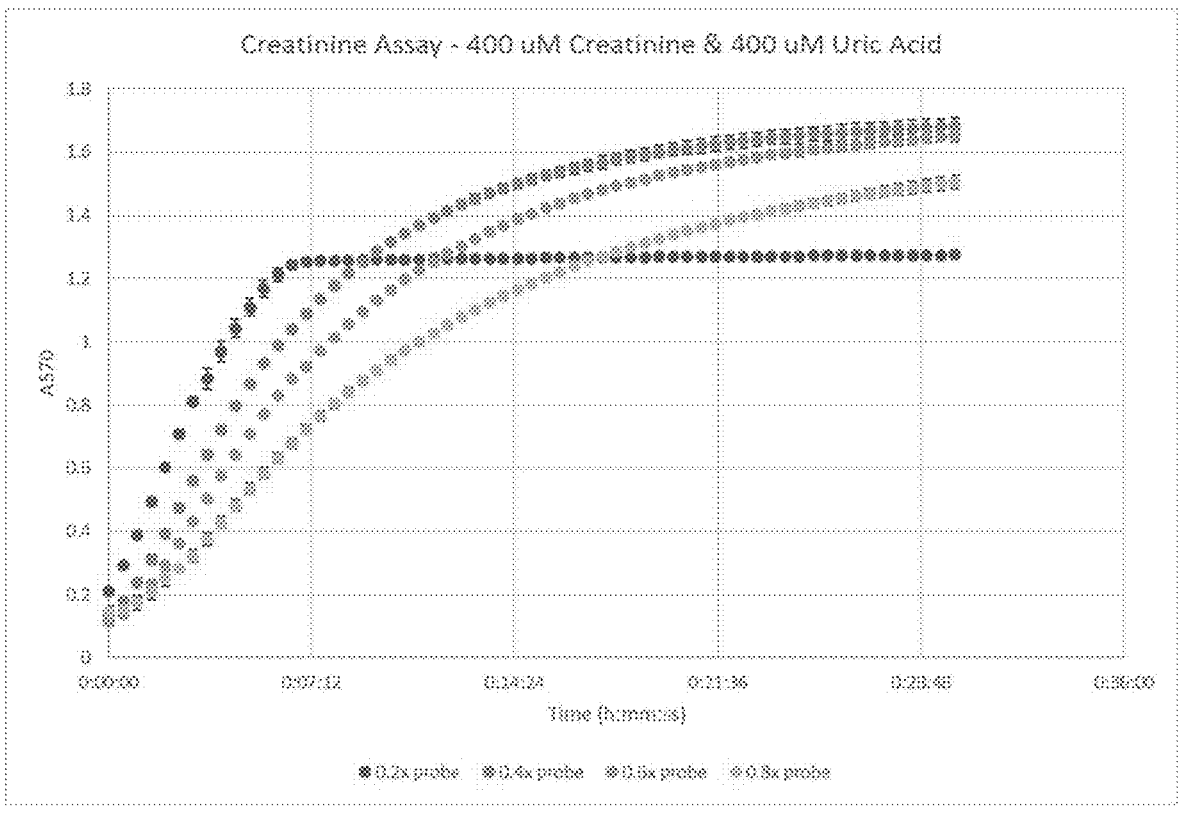
FIG. 10 illustrates stabilization of absorbance/reporter, in accordance with an exemplary embodiment of the present invention.
Figure 11:
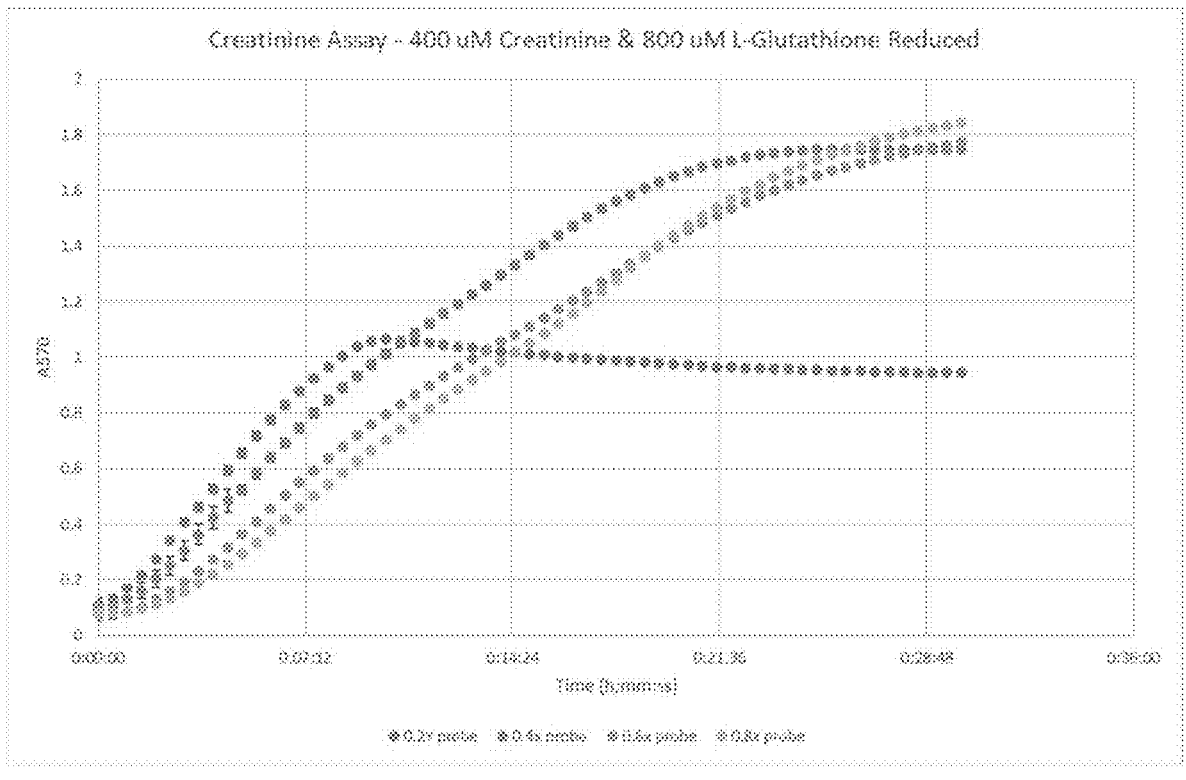
FIG. 11 illustrates stabilization of absorbance/reporter, in accordance with an exemplary embodiment of the present invention.
Figure 12:
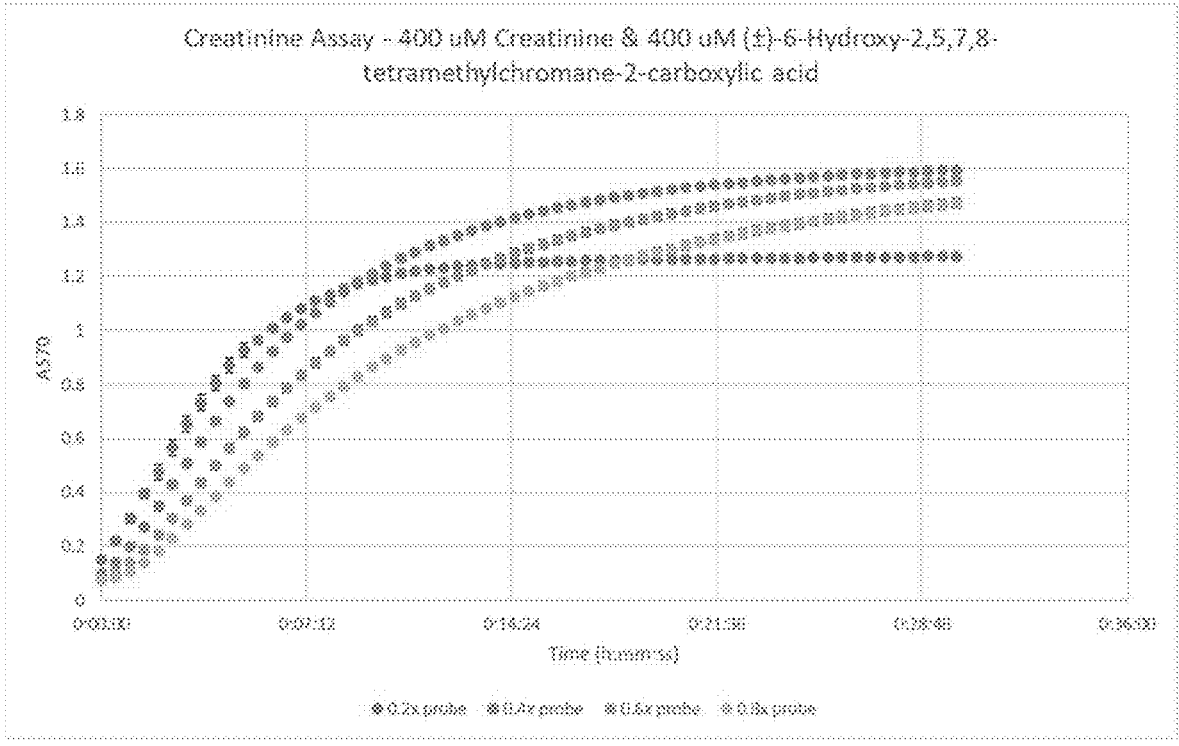
FIG. 12 illustrates stabilization of absorbance/reporter, in accordance with an exemplary embodiment of the present invention.
Figure 13:
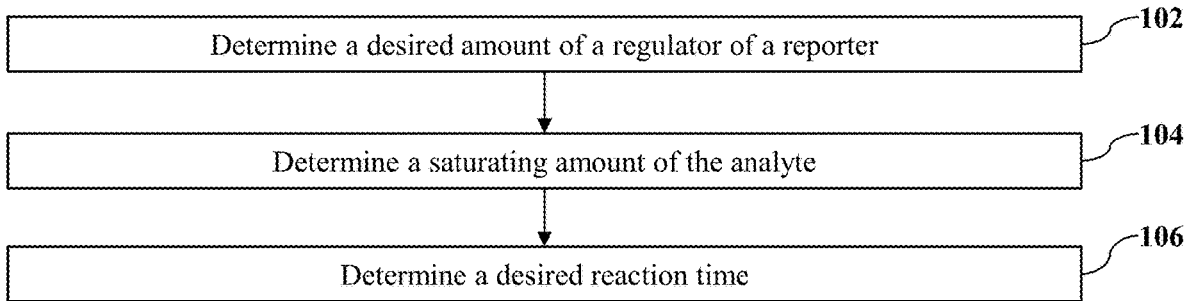
FIG. 13 illustrates a method of generating a diagnostic tool for measuring an unknown amount of an analyte in a biological sample using a cell-free extract
Figure 14:
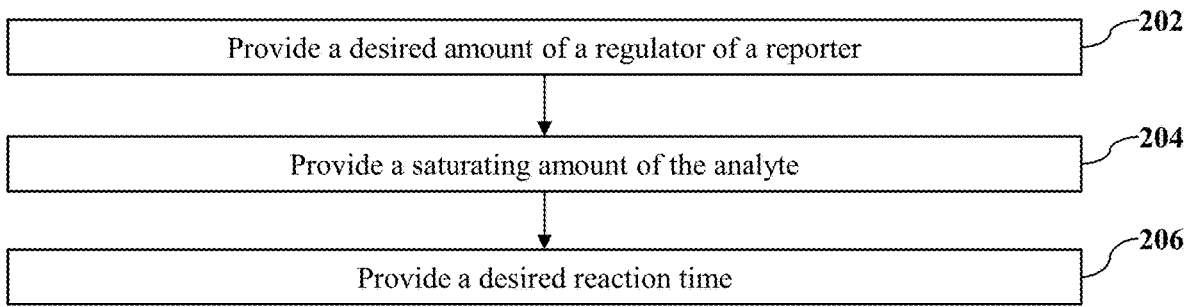
FIG. 14 illustrates a method for generating a range of visible colors in serum samples with unknown amounts of an analyte
Figure 15:
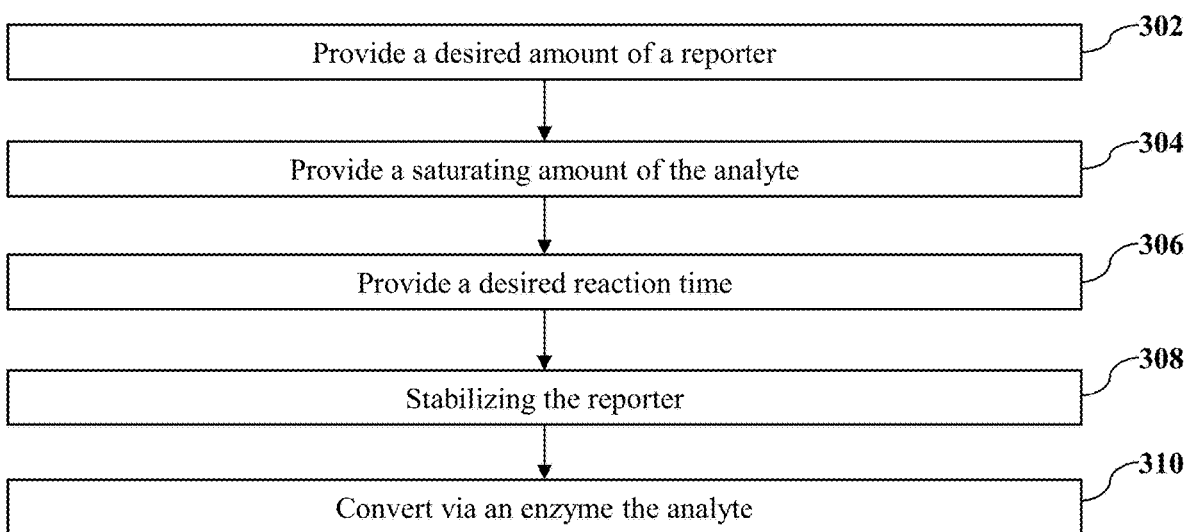
FIG. 15 illustrates a method for generating a range of visible colors in serum samples with unknown amounts of an analyte

As specified in the Background Section and in more detail below, there is a great need in the art to identify technologies for quantitative diagnostic systems and tools for use in complex solutions and use this understanding to develop novel quantitative diagnostic systems and methods for reducing or eliminating inter-sample variability in measuring analytes with complex samples such as biological fluids and water by providing a generalizable parallel calibration strategy.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive," or it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

Definitions

The term "expression" as used herein is defined as the transcription and/or translation of a particular nucleotide sequence driven by its promoter. The amount of expression may be measured by using any method known to those of skill in the art to be suitable. For example, mRNA expression of the protein of interest may be detected using northern blots or their polypeptide products may be identified using immunoassays. Alternatively, transcription-based assays using reporter genes may be used as described in U.S. Pat. No. 5,436,128, herein incorporated by reference.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. In cell-free systems, PCR products may be used in a similar manner as expression vectors and may contain the same expression control systems and cis-acting expression elements.

The term "reporter" as used herein includes a reporter gene that is attached to a genetic element that is regulated, directly or indirectly, by a regulator. The reporter gene is operatively connected to the genetic element such that the expression of the reporter gene serves as an indication of the regulator's activity. The term "reporter" as used herein includes more generally chemical probes designed to produce one or more color shifts.

Non-limiting examples of the genetic element include a promoter (e.g., an inducible promoter), a binding site for a repressor, a binding site for an activator, a binding site for a regulatory molecule, a binding site for a transcription factor, a binding site for a ribosome, and translation regulatory elements (such as for example and without limitation, hairpin RNA sequences and small regulatory RNAs such as siRNA and microRNA). The genetic element can also include enhancer sequences that modulate the activity of the promoter, or control sequences that modulate the activity or efficiency of the RNA polymerase that recognizes the promoter, or control sequences that are recognized by effector molecules. The genetic element can also include sequences that modulate the activity or efficacy of the ribosome, or control sequences that are recognized by effector molecules, or control sequences that modulate protein levels post-translationally (such as, for example, tags that induce degradation by proteases).

The reporter gene produces a measurable or quantifiable gene product, such as a colorimetric gene product. As used herein, a colorimetric gene product includes, e.g., a fluorescent gene product, a luminescent gene product, a colored gene product that is visible to the naked eye, and a gene product that is optically detectable at a certain wavelength. The colorimetric gene product may be directly produced by the reporter gene (e.g., green fluorescent protein, GFP) or the colorimetric gene product may be indirectly produced by the reporter gene, such as by enzymatic activity (e.g., β-galactosidase cleaves the yellow substrate chlorophenol red-β-D-galactopyranoside (CPRG) to produce a purple product chlorophenol red (CPR); gradations of the purple color can be produced by increasing activity of the β-galactosidase).

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology,* John Wiley & Sons, Inc. (1994); among others.

In an exemplary embodiment of the present disclosure, there is provided a method 100 of generating a diagnostic tool for measuring an unknown amount of an analyte in a biological sample using a cell-free extract (CFE). The method can include: determining 102 a desired amount of a regulator of a reporter, determining 104 a saturating amount of the analyte, and determining 106 a desired reaction time. The diagnostic tool can include a plurality of reference points, each reference point being a distinct color and corresponding to a different amount of the analyte. The desired amount of the regulator of the reporter, the saturating amount of the analyte, and the desired reaction time can be determined such that when the unknown amount of the analyte is combined with the biological sample, the CFE, and the desired amount of the regulator of the reporter for the desired reaction time, a colorimetric gene product is generated having a color corresponding to a color of a first reference point in the plurality of reference points containing the biological sample, the CFE, the saturating amount of analyte, and the desired amount of the regulator of the reporter, the first reference point associated with an amount of the analyte about equal to the unknown amount of analyte.

In some embodiments, the method can further include obtaining a plurality of outputs from a plurality of varying levels of the regulator and comparing the plurality of outputs to a plurality of outputs from a plurality of varying levels of analyte at a fixed level of regulator.

In some embodiments, the biological sample is one or more of: blood, serum, plasma, urine, saliva, tears, mucus, lymph, interstitial fluid, cerebrospinal fluid, pus, breast milk, and amniotic fluid.

In some embodiments, the analyte can include one of creatinine, creatine, or sarcosine.

An exemplary embodiment of the present invention discloses a method 200 for generating a range of visible colors in serum samples with unknown amounts of an analyte by addition of a small molecule, wherein the small molecule displaces an interfering molecule from one or more of a regulator, a reporter, and a molecule acted on by the reporter.

The method can include determining 202 a desired amount of a regulator of a reporter, determining 204 a saturating amount of the analyte, and determining 206 a desired reaction time. The desired amount of the regulator of the reporter, the saturating amount of the analyte, and the desired reaction time can be determined such that when the unknown amount of the analyte is combined with the serum and the desired amount of the regulator of the reporter for the desired reaction time, a colorimetric gene product is generated having a color corresponding to a color of a first reference point in a plurality of reference points containing the serum, the saturating amount of analyte, and the desired amount of the regulator of the reporter, the first reference point associated with an amount of the analyte about equal to the unknown amount of analyte. The method can be configured to reduce or eliminate inter-sample variability.

In some embodiments, the reporter can include a linear fragment of DNA, the linear fragment of DNA can include the regulator and a reporter gene operatively linked to a genetic element that is regulated by the regulator.

In some embodiments, the reporter can include a first plasmid containing a transcriptional regulator and a second plasmid containing a reporter gene operatively linked to a promoter, wherein expression from the promoter is controlled by the amount of the regulator.

In some embodiments, the method can further include converting via an enzyme the analyte, wherein the converted analyte is configured to allow binding of the regulator and the promoter thus activating transcription of the reporter gene.

In some embodiments, the analyte can include one of creatinine, creatine, or sarcosine.

In some embodiments, the regulator of the reporter can include a sarcosine-responsive transcription factor from *Pseudomonas aeruginosa* (SouR).

An exemplary embodiment of the present invention discloses a method 300 for generating a range of visible colors in serum samples with unknown amounts of an analyte by addition of a small molecule, wherein the small molecule displaces an interfering molecule from one or more of a regulator, a reporter, and a molecule acted on by the reporter. The method can include providing 302 a desired amount of a regulator of a reporter, providing 304 a saturating amount of the analyte, providing 306 a desired reaction time, and stabilizing 308 the reporter. The desired amount of the regulator of the reporter, the saturating amount of the analyte, and the desired reaction time can be determined such that when the unknown amount of the analyte is combined with the serum, and the desired amount of the regulator of the reporter for the desired reaction time, the reporter generates a color corresponding to a color of a first reference point in the plurality of reference points containing the serum, the saturating amount of analyte, and the desired amount of the regulator of the reporter, the first reference point associated with an amount of the analyte about equal to the unknown amount of analyte. The method can be configured to reduce or eliminate inter-sample variability.

In some embodiments, the reporter comprises a limited chemical probe.

In some embodiments, the chemical probe can include a fluorogenic peroxidase substrate.

In some embodiments, the reporter can include a linear fragment of DNA, the linear fragment of DNA including the regulator and a reporter gene operatively linked to a genetic element that is regulated by the regulator.

In some embodiments, the reporter can include a first plasmid containing a transcriptional regulator and a second plasmid containing a reporter gene operatively linked to a promoter, wherein expression from the promoter is controlled by the amount of the regulator.

In some embodiments, the method can further include converting 310 via an enzyme the analyte, wherein the converted analyte is configured to allow binding of the regulator and the promoter thus activating transcription of the reporter gene.

In some embodiments, the analyte can include one of creatinine, creatine, or sarcosine.

In some embodiments, the regulator of the reporter can include a sarcosine-responsive transcription factor from *Pseudomonas aeruginosa* (SouR).

In some embodiments, stabilizing the reporter can include providing a stabilizing compound.

In some embodiments, the stabilizing compound can include one or more of: doxorubicin, vitamin C, citric acid, vitamin E, uric acid, L-glutathione (reduced), and (±)-6-Hydroxy-2,5,7,8-tetramethylchromane-2-carboxylic acid.

EXAMPLES

There are no low-cost, minimal-equipment approaches to measure creatinine, creatine, or sarcosine at the point of care in a quantitative fashion. Existing approaches at least require a plate reader for quantification of colorimetric output. In the disclosure herein, the approach enables visual interpretation based on hue rather than color intensity, allowing a semi-quantitative approach that is more field-friendly by virtue of not requiring any equipment.

Chronic kidney disease (CKD) is a common comorbidity with HIV that must be carefully monitored. Treatment of CKD can be burdensome to the patient, involving regular renal function monitoring and potentially including dialysis; these treatments may be more difficult or impossible in low- and middle-income countries (LMICs). As CKD progresses it can irreparably damage kidneys, which can result in either the need for a kidney transplant or progression to end stage renal disease, a condition in which the organ fails and that often leads to patient death. Routine monitoring of renal function is therefore recommended by clinical practice guidelines for persons living with HIV prior to initiating most antiretroviral and other common therapies, to avoid causing or accelerating the development of CKD.

Cardiovascular disease is also a common co-morbidity of HIV, due at least in part to HIV-related inflammation and immune dysregulation, and assessment of kidney function is important for safely prescribing pharmacotherapy to treat and control hypertension, ischemic heart disease, heart failure, and other cardiovascular diseases. For example, several commonly-used blood pressure lowering drugs (e.g. ACE inhibitors, angiotensin receptor blockers, diuretics, and mineralocorticoid receptor antagonists, all of which are on the World Health Organization's Model List of Essential Medicines) are associated with increased risk for acute kidney injury. As a result, in areas where access to assays for renal function is unavailable or infeasible, doctors often avoid prescribing these drugs and refer patients up to higher levels of a health system, which reduces linkage to care.

The difficulties faced by people in LMICs with limited healthcare infrastructure in accessing the resources required for regular renal function monitoring place a substantial burden on this vulnerable population and the healthcare facilities that serve them. Providing an easier way to assess renal function would provide health care workers more options for managing HIV itself, as well as common comorbidities associated with HIV.

In some diagnostic approaches, small molecules and proteins are used as biomarkers of various diseases. For example, early diagnosis of kidney disease can use the following example biomarkers: albumin, creatinine, cystatin C, transferrin (Tf), interleukin-18 (IL-18), retinol binding protein 4 (RBP4), kidney injury molecule-1 (KIM-1), N-acetyl-β-D-glucosaminidase (NAG), tissue inhibitor of metalloporteinase 2 (TIMP2), and neutrophil gelatinase-associated lipocalin (NGAL). Specifically, creatinine is a biomarker for renal function whose levels play an important role in determining the course of treatment in a number of diseases.

In addition to creatinine, sarcosine is also believed to a be a biomarker for a number of diseases. In particular, sarcosine is believed to be a biomarker for cancer. The ability to measure sarcosine quantitatively in an inexpensive fashion would allow for its widespread use as a screening technique.

In some embodiments, an existing laboratory assay kit for creatinine (a biomarker for renal function) is adapted in a number of different ways. In one aspect, the kit can be adapted via direct modification of the kit to approximate a self-calibrating system. In certain embodiments, the kit can be adapted by integrating kit components with a cell-free system to enable an easier-to-read quantitative output that is robust to matrix effects.

The existing assay is a purely enzymatic approach that translates the concentration of creatinine into a colorimetric change of varying intensity. It contains two enzymes. The first enzyme, creatininase, catalyzes the conversion of creatinine to creatine. The second enzyme, creatinase, catalyzes creatine to sarcosine. This bioconversion aspect of the assay can be maintained in both of the embodiments. In the existing assay, the sarcosine is then oxidized by sarcosine oxidase, generating hydrogen peroxide in the process. The fluorogenic peroxidase substrate Amplex Red, hereafter referred to as the "probe", interacts with the generated hydrogen peroxide in the presence of horseradish peroxidase to produce the red-fluorescent product resorufin (see Yamkamon et al. Simultaneous determination of sarcosine and its related metabolites by gas chromatography-tandem mass spectrometry for prostate cancer diagnosis, EXCLI Journal, 2018). Resorufin accumulation leads to a visible color change with a linear response over physiological serum creatinine concentrations. However, there is significant day-to-day variability of unknown origin that affects the amplitude of the output, thus requiring (per manufacturer's instructions) a calibration curve to be run with every sample or batch of samples and complicating field deployment.

In certain embodiments of the disclosed invention, the existing assay can be taken in its entirety and titrated down the amount of probe (fluorogenic peroxidase substrate, Amplex Red) so as to produce a sample-specific calibration curve. The probe concentration that corresponds with specific creatinine concentrations in calibration tests can be first identified using defined chemical mixtures and then implemented in a serum sample matrix to validate the sample-specific calibration curve. Preliminary work showed that creatinase and creatininase, the originally planned limiting reagents, were so fast that it made more sense to instead limit the probe. This method yields a set of reactions to which patient sample can be added, and regardless of the sample levels of creatinine, the calibration spots will all correspond to defined levels of creatinine. The reaction with excess probe can then be visually compared to the calibration spots to determine the creatinine level. In particular, a shift from colorless to red may be useful for a presence-absence or binary diagnostic test. For more accurate monitoring of intensity of color, a plate reader (e.g., spectrophotometer or fluorescence reader) can be used.

Certain aspects of the invention allow for accurately quantifying serum creatinine. In some embodiments, adapting the existing assay can include applying an approach for field-deployable quantification of biosensor output. For example, WO Publication No. 2020/051268 A1 to Styczynski, which is hereby incorporated herein by reference, describes systems, methods, and diagnostic tools for quantifying analytes in aqueous solutions or biological fluid samples with sample-specific calibration and colorimetric or detectable output.

In any of the embodiments disclosed herein, to make the assay quantitative and field-deployable, an alternate reporter system can be implemented that yields a color shift, for instance, from yellow to orange to red to purple. In some embodiments, the color shift could even be aligned to creatinine levels corresponding to different stages of chronic kidney disease. This color shift can yield an output much more easily interpreted with the naked eye, as for most people it is much easier to visually distinguish hue than to distinguish intensity. In certain embodiments, a cell-free diagnostic is implemented, that includes cell-free zinc diagnostics. (see McNerney et al. Dynamic and tunable metabolite control for robust minimal-equipment assessment of serum zinc, Nature Communications, 2019).

In some embodiments, the enzymes from the existing assay (creatininase and creatinase) can be included to stoichiometrically convert all creatinine to sarcosine. In certain embodiments, analogs of creatininase and/or creatinase can be used. To this, a sarcosine-responsive transcription factor from Pseudomonas aeruginosa, SouR can be added. In the presence of sarcosine, this protein binds to its promoter, activating transcription. In some embodiments, beta-galactosidase (LacZ) can be under control of a SouR-regulated promotor. When induced, LacZ can act on the yellow substrate chlorophenol red-beta-D-galactopyranoside (CPRG) to form the purple (at the operating pH) molecule chlorophenol red (CPR), with mixtures of the two forming varying shades of red and orange. At low sarcosine levels, the substrate will remain yellow, but at higher sarcosine levels, more CPRG is cleaved, with a color gradient that is easier to visually read than the intensity of a color. The lowest A580 readings correspond with yellow reactions (the color of CPRG), and as the A580 increases, and the reaction color turns different shades of orange, red, and purple (the color of CPR).

In some embodiments, a colorimetric response can be quantified based on added creatininase, creatinase, and/or sarcosine. At early time points, there was no detectable absorbance of the purple substrate CPR at tested [sarcosine], and reactions appeared yellow (the color of CPRG). As the reactions proceeded, they produced CPR at different rates based on the concentration of sarcosine in the reaction, with the maximal differences visible between 60 and 70 minutes. An ideal assay readout time would yield outputs spanning a wide range of absorbances across as much of the [sarcosine] range as possible.

In any of the embodiments disclosed herein, the analyte being measured in the biological sample with the CFE can be creatinine, creatine, and/or sarcosine. In any of the embodiments disclosed herein, the reporter can comprise a first plasmid containing a transcriptional regulator SouR and a second plasmid containing a reporter gene operatively linked to a SouR-regulated promoter, wherein expression from the SouR-regulated promoter is controlled by the amount of the transcriptional regulator SouR.

In any of the embodiments disclosed herein, the biological sample can be a biological fluid sample. In any of the embodiments disclosed herein, the biological fluid sample can be selected from the group consisting of blood, serum, plasma, urine, saliva, tears, mucus, lymph, interstitial fluid, cerebrospinal fluid, pus, breast milk, and amniotic fluid.

In any of the embodiments disclosed herein, the reporter can be plasmid-based or can be present on a linear fragment of DNA. In any of the embodiments disclosed herein, the plasmid-based reporter can comprise the regulator and a reporter gene operatively linked to a genetic element that is regulated by the regulator. In any of the embodiments disclosed herein, the linear fragment of DNA can comprise the regulator and a reporter gene operatively linked to a genetic element that is regulated by the regulator. In any of the embodiments disclosed herein, the regulator can comprise a transcription factor, a repressor, and an activator. In any of the embodiments disclosed herein, the genetic element can comprise a promoter, one or more regulatory protein binding sites, one or more repressor binding sites, and one or more transcription factor binding sites.

In any of the embodiments disclosed herein, the reporter gene can produce a quantifiable or detectable gene product. In any of the embodiments disclosed herein, the quantifiable or detectable gene product can be a colorimetric gene product. In any of the embodiments disclosed herein, the colorimetric gene product can comprise a fluorescent protein, a luminescent protein, a colored protein, a protein that produces a detectable and quantifiable product, and a protein that can be quantified by measuring its absorbance at a wavelength. In any of the embodiments disclosed herein, the quantifiable or detectable gene product can be produced directly by the reporter gene. In any of the embodiments disclosed herein, the quantifiable or detectable gene product can be produced indirectly by the reporter gene, e.g., by enzymatic activity of the reporter gene.

Implementing this sensor can use a cell-free expression system (CFE), in which transcriptional and translational machinery are harvested from *E. coli* in a cell lysate and used to express proteins from plasmid DNA.

In some embodiments, the systems and methods described herein can present advantages and improvements over existing methods, devices or materials in several ways, such as, for example, reducing cost, eliminating inter-sample variability, and increased accessibility. Current renal function monitoring involves a laboratory visit during which a trained phlebotomist draws a blood sample. The serum is then separated from the blood by technicians using specialized equipment. Creatinine, an established biomarker that accumulates in the serum of patients with decreased renal function, is then quantified, often using the Jaffe method. The Jaffe method is a clinical laboratory procedure involving the addition of picric acid to the serum, which reacts with creatinine to create a colorimetric output measured by expensive analytical equipment. A creatinine test is commonly required not only for CKD but also for routine, urgent, emergency, and even critical care for a range of conditions. Serum creatinine testing thus has been included on the World Health Organization's Essential Diagnostics List.

As described above, the expensive equipment required for the Jaffe method, combined with its susceptibility to interferents in the patient serum sample, make it unsuitable for use at the point of care or in low-to-middle-income countries (LMICs) lacking substantial clinical testing infrastructure. The recently adopted reference method, isotope dilution mass spectrometry, addresses the issue of interferents but only aggravates the cost and complexity issues by requiring a mass spectrometer for creatinine measurement. Lack of access to creatinine testing impacts patient health via missed or delayed diagnoses which could lead to prolonged or worsened symptoms, and may also lead to treatment avoidance or inertia. As untreated CKD or other HIV co-morbidities can lead to patient health deterioration and death, increasing access to renal function monitoring via serum creatinine testing could substantially improve patient outcomes.

Some point-of-care devices, such as iSTAT by Abbott, have recently been developed for creatinine measurements and have been tested outside of health care facilities (e.g. in US barbershops). However, these approaches have important limitations for limited resource settings, including: 1) requirement of venipuncture, with associated training and collection materials; 2) heat labile consumables that require cold chain storage and transportation; and 3) high per-unit cost of both the instrument and its consumables. Each of these characteristics substantially decreases the utility of the assay in LMICs, and taken together they make the approach largely inviable for use in LMICs. Moreover, measurements of renal function biomarkers like creatinine must be quantitative, which is hindered by inter-individual variation, known as "matrix effects", that interfere with the measurement of target compounds. These matrix effects are prevalent even in sophisticated instruments in clinical laboratories but are often more prominent in point-of-care tests that are designed for deployment with minimal equipment and resources. Taken together, these limitations form a complex challenge that, if overcome, would have a substantial impact on the delivery of healthcare to HIV patients in LMICs.

Creation of a CFE-based reporter would significantly decrease costs compared to the enzymatic assay while providing results on a similar time scale. In fact, the two initial enzymes in the test can actually also be expressed in the CFE-system, substantially reducing the cost of reagents. In some examples, CFE-based biosensors can cost as little as a few cents per test and yield results in under an hour (see McNerney et al. 2019). Additionally, CFE-based sensors can be lyophilized onto a paper substrate for eventual rehydration by patient serum samples, which removes the need for cold chain shipment and storage and makes the sensor promising for use in low-resource areas.

An additional benefit of the CFE-based sensor is that when properly designed, the sensor compensates for matrix effects, which is the inter-sample variability of results due to compounds in the sample other than the target—a phenomenon that confounds quantification. CFE-based approaches can compensate for matrix effects by using the sample itself for "calibration curve"-like reactions. This is accomplished by having each of the calibration reactions saturated in the target (creatinine) but with varying levels of a limiting regulatory component (SouR) and mapping those outputs to output from different levels of creatinine at a fixed level of regulator. This yields sample-specific calibration reactions of different colors to which the user can match their actual sample results, allowing visually and quantitatively inter- pretable results.

Furthermore, in order to reduce the patient-to-patient variability in readouts, also known as matrix effects, where the molecule being measured may appear to be at a different concentration only due to interferences from other constitu- ents of the solution, the inventors identified that the appro- priate reagent to limit was not the enzymes in the chemical assay, but rather the chemical probe. However, when the concentration of the chemical probe was reduced to a low level to enable the calibration approach, a side reaction happened where probe that has been transformed from colorless into colored form undergoes a second reaction that brings it back to a colorless form. This made the signal "decay" and thus would lead to an underreporting of the target molecule's concentration.

The inventors showed that by adding antioxidants at different concentrations, they were able to avoid the unde- sired transformation of colored probe product into colorless side product, and thus get accurate readings from the assay. Vitamin C, citric acid, Vitamin E, uric acid, L-glutathione (reduced), and (±)-6-Hydroxy-2,5,7,8-tetramethylchro- mane-2-carboxylic acid have been shown by the inventors to achieve this effect of preventing the decay of probe signal, thus allowing use of the probe at low concentrations and enabling the application of the parallel calibration scheme.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodi- ments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitio- ners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:
1. A method of generating a diagnostic tool for measuring an unknown amount of an analyte in a biological sample using a cell-free extract (CFE), the diagnostic tool compris- ing a plurality of reference points, each reference point being a distinct color and corresponding to a different amount of the analyte, the method comprising:

determining a desired amount of a regulator of a reporter, the regulator comprising a sarcosine-responsive tran- scription factor from *Pseudomonas aeruginosa* (SouR); determining a saturating amount of the analyte; and determining a desired reaction time;
wherein the desired amount of the regulator of the reporter, the saturating amount of the analyte, and the desired reaction time are determined such that when the unknown amount of the analyte is combined with the biological sample, the CFE, and the desired amount of the regulator of the reporter for the desired reaction time, a colorimetric gene product is generated having a color corresponding to a color of a first reference point in the plurality of reference points containing the biological sample, the CFE, the saturating amount of analyte, and the desired amount of the regulator of the reporter, the first reference point associated with an amount of the analyte about equal to the unknown amount of analyte.
2. The method of claim 1 further comprising:
obtaining a plurality of outputs from a plurality of varying levels of the regulator; and
comparing the plurality of outputs to a plurality of outputs from a plurality of varying levels of analyte at a fixed level of regulator.
3. The method of claim 1, wherein the biological sample is one or more of: blood, serum, plasma, urine, saliva, tears, mucus, lymph, interstitial fluid, cerebrospinal fluid, pus, breast milk, and amniotic fluid.
4. The method of claim 1, wherein the analyte comprises one of creatinine, creatine, or sarcosine.
5. A method for generating a range of visible colors in serum samples with unknown amounts of an analyte by addition of a small molecule, wherein the small molecule displaces an interfering molecule from one or more of a regulator, a reporter, and a molecule acted on by the reporter, the method comprising:
providing a desired amount of a regulator of a reporter, the regulator comprising a sarcosine-responsive transcrip- tion factor from *Pseudomonas aeruginosa* (SouR);
providing a saturating amount of the analyte; and
providing a desired reaction time;
wherein:
the desired amount of the regulator of the reporter, the saturating amount of the analyte, and the desired reaction time are determined such that when the unknown amount of the analyte is combined with the serum and the desired amount of the regulator of the reporter for the desired reaction time, a colorimetric gene product is generated having a color correspond- ing to a color of a first reference point in a plurality of reference points containing the serum, the satu- rating amount of analyte, and the desired amount of the regulator of the reporter, the first reference point associated with an amount of the analyte about equal to the unknown amount of analyte; and
the method is configured to reduce or eliminate inter- sample variability.
6. The method of claim 5, wherein the reporter comprises a linear fragment of DNA, the linear fragment of DNA comprising the regulator and a reporter gene operatively linked to a genetic element that is regulated by the regulator.
7. The method of claim 5, wherein the reporter comprises a first plasmid containing a transcriptional regulator and a second plasmid containing a reporter gene operatively linked to a promoter, wherein expression from the promoter is controlled by the amount of the regulator.

8. The method of claim 7 further comprising:

converting via an enzyme the analyte;

wherein the converted analyte is configured to allow binding of the regulator and the promoter, thus activating transcription of the reporter gene.

9. The method of claim 5, wherein the analyte comprises one of creatinine, creatine, or sarcosine.

10. A method for generating a range of visible colors in serum samples with unknown amounts of an analyte by addition of a small molecule, wherein the small molecule displaces an interfering molecule from one or more of a regulator, a reporter, and a molecule acted on by the reporter, the method comprising:

providing a desired amount of a reporter, the reporter comprising one or more plasmids;

providing a saturating amount of the analyte;

providing a desired reaction time; and stabilizing the reporter, the stabilizing comprising providing a stabilizing compound selected from the group consisting of doxorubicin, vitamin C, citric acid, vitamin E, uric acid, L-glutathione (reduced), and (±)-6-Hydroxy-2,5,7,8-tetramethylchromane-2-carboxylic acid and combinations thereof;

wherein:

the desired amount of the reporter, the saturating amount of the analyte, and the desired reaction time are determined such that when the unknown amount of the analyte is combined with the serum and the desired amount of the reporter for the desired reaction time, the reporter generates a color corresponding to a color of a first reference point in a plurality of reference points containing the serum, the saturating amount of analyte, and the desired amount of the reporter, the first reference point associated with an amount of the analyte about equal to the unknown amount of analyte; and the method is configured to reduce or eliminate inter-sample variability.

11. The method of claim 10, wherein the reporter comprises a limited chemical probe.

12. The method of claim 11, wherein the chemical probe comprises a fluorogenic peroxidase substrate.

13. The method of claim 10 further comprising:

providing the desired amount of a regulator of a reporter; wherein:

the reporter comprises a linear fragment of DNA, the linear fragment of DNA comprising the regulator and a reporter gene operatively linked to a genetic element that is regulated by the regulator; and the desired amount of the regulator of the reporter, the saturating amount of the analyte, and the desired reaction time are determined such that when the unknown amount of the analyte is combined with the serum and the desired amount of the regulator of the reporter for the desired reaction time, a colorimetric gene product is generated having a color corresponding to a color of a first reference point in a plurality of reference points containing the serum, the saturating amount of analyte, and the desired amount of the regulator of the reporter, the first reference point associated with an amount of the analyte about equal to the unknown amount of analyte.

14. The method of claim 10 further comprising:

providing the desired amount of a regulator of a reporter; wherein:

the reporter comprises a first plasmid containing a transcriptional regulator and a second plasmid containing a reporter gene operatively linked to a promoter, wherein expression from the promoter is controlled by the amount of the regulator, and the desired amount of the regulator of the reporter, the saturating amount of the analyte, and the desired reaction time are determined such that when the unknown amount of the analyte is combined with the serum and the desired amount of the regulator of the reporter for the desired reaction time, a colorimetric gene product is generated having a color corresponding to a color of a first reference point in a plurality of reference points containing the serum, the saturating amount of analyte, and the desired amount of the regulator of the reporter, the first reference point associated with an amount of the analyte about equal to the unknown amount of analyte.

15. The method of claim 14 further comprising:

converting via an enzyme the analyte;

wherein the converted analyte is configured to allow binding of the regulator and the promoter, thus activating transcription of the reporter gene.

16. The method of claim 10, wherein the analyte comprises one of creatinine, creatine, or sarcosine.

17. The method of claim 16, wherein the regulator of the reporter comprises a sarcosine-responsive transcription factor from *Pseudomonas aeruginosa* (SouR).

* * * * *